US012260954B2

(12) United States Patent
Hanrahan et al.

(10) Patent No.: US 12,260,954 B2
(45) Date of Patent: *Mar. 25, 2025

(54) CONNECTIVITY INFRASTRUCTURE FOR A TELEHEALTH PLATFORM

(71) Applicant: TELADOC HEALTH, INC., Purchase, NY (US)

(72) Inventors: Kevin Hanrahan, Santa Barbara, CA (US); John Schentrup, Lompoc, CA (US); Parixit Kaira, Santa Barbara, CA (US); Marco Pinter, Santa Barbara, CA (US); John Cody Herzog, Santa Barbara, CA (US); Blair Whitney, Santa Barbara, CA (US); Jonathan Southard, Santa Barbara, CA (US)

(73) Assignee: TELADOC HEALTH, INC., Purchase, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/138,574

(22) Filed: Apr. 24, 2023

(65) Prior Publication Data

US 2023/0260635 A1 Aug. 17, 2023

Related U.S. Application Data

(63) Continuation of application No. 16/114,091, filed on Aug. 27, 2018, now Pat. No. 11,636,944.
(Continued)

(51) Int. Cl.
*G16H 40/20* (2018.01)
*A61B 5/00* (2006.01)
(Continued)

(52) U.S. Cl.
CPC .......... *G16H 40/20* (2018.01); *A61B 5/0002* (2013.01); *G06F 11/3055* (2013.01);
(Continued)

(58) Field of Classification Search
CPC ........ G16H 40/20; G16H 80/00; H04L 67/54; G06F 11/3055
(Continued)

(56) References Cited

U.S. PATENT DOCUMENTS 9,374,363 B1 * 6/2016 Paczkowski ............ G06F 21/32
2010/0198608 A1 * 8/2010 Kaboff .................... G16H 40/67
715/741

FOREIGN PATENT DOCUMENTS

GB 2477857 A * 8/2011 ............... B62B 7/14

OTHER PUBLICATIONS

Sadeghi, Payam; A Mashup Based Framework for Multi Level Healthcare Interoperability; University of Ottawa (Canada). ProQuest Dissertations Publishing, 2011. MR79673. (Year: 2011).*

* cited by examiner

*Primary Examiner* — Hiep V Nguyen

(57) ABSTRACT

A secure, reliable telehealth delivery platform that also provides flexibility and scalability. The platform includes a plurality of geographically dispersed communication servers that facilitate communication sessions between remotely located patients and healthcare providers over a public communications network. The platform includes a connectivity server that manages access among users and locations. The platform also includes a monitoring server that monitors the health and usage of devices coupled to the network and proactively identifies issues requiring intervention before service interruptions occur.

18 Claims, 2 Drawing Sheets

Related U.S. Application Data

(60) Provisional application No. 62/550,514, filed on Aug. 25, 2017.

(51) Int. Cl.
| | |
|---|---|
| *G06F 11/30* | (2006.01) |
| *G16H 10/60* | (2018.01) |
| *G16H 50/20* | (2018.01) |
| *G16H 50/30* | (2018.01) |
| *G16H 80/00* | (2018.01) |
| *H04L 67/54* | (2022.01) |

(52) U.S. Cl.
CPC .............. *G16H 10/60* (2018.01); *G16H 50/20* (2018.01); *G16H 50/30* (2018.01); *G16H 80/00* (2018.01); *H04L 67/54* (2022.05)

(58) Field of Classification Search
USPC .......................................................... 705/2
See application file for complete search history.

CONNECTIVITY INFRASTRUCTURE FOR A TELEHEALTH PLATFORM

CROSS-REFERENCE TO RELATED APPLICATIONS

This application is a continuation of U.S. application Ser. No. 16/114,091, filed Aug. 27, 2018, which claims priority to U.S. provisional application No. 62/550,514, filed Aug. 25, 2017, the contents of which are hereby incorporated by reference.

TECHNICAL FIELD

The present technology pertains to telehealth systems, and more specifically to a network and connectivity infrastructure for a telehealth platform.

BACKGROUND

Telehealth or telemedicine is the practice of conducting consultations between patients and caregivers in different locations. Telemedicine technologies allow physicians and other care providers to see, hear, communicate with, diagnose, instruct or otherwise provide care to remotely located patients. Existing telemedicine technologies range from simple audio communication devices such as telephones to videoconferencing systems to remotely controlled mobile videoconferencing devices with autonomous navigation capabilities. One such remotely controlled device is that marketed under the trademark RP-VITA or INTOUCH VITA by INTOUCH TECHNOLOGIES, INC. of Goleta, California Other telemedicine devices or "endpoints" offered by INTOUCH TECHNOLOGIES, INC., include the cart-based INTOUCH LITE, INTOUCH VICI, and INTOUCH VANTAGE, the portable INTOUCH EXPRESS and INTOUCH VIEWPOINT or VIEWPOINT TABLET, and the ultra-portable INTOUCH TV, which can be coupled to any television to create a telemedicine endpoint. In addition, any computing device running INTOUCH VIEWPOINT software or a web browser directed to the INTOUCH cloud-based CONSUMER portal can be used to conduct a telemedicine session.

Each of these devices, which are typically situated in the vicinity of a patient, includes at least one camera, monitor, microphone, and speaker that enable two-way audiovisual communication between the patient and the remote physician. In conjunction with a managed network, cloud-based documentation platform, and a purpose-built user interface provided to the physician via a laptop, desktop, or smartphone, these devices allow physicians to communicate with, examine, and diagnose even high-acuity patients from a remote location, as well as retrieve, edit, and store patient medical records and medical imaging from disparate healthcare facility IT systems and electronic health record systems.

Many organizations that wish to offer telehealth services struggle to establish a delivery platform that is both secure and reliable but also flexible and scalable. Complex webs of Virtual Private Networks (VPNs) may provide secure communications among care locations within a healthcare organization, but VPNs tend to suffer from reliability issues that may prevent or otherwise interrupt telehealth sessions at critical times. Moreover, pre-established VPNs generally do not permit sessions with entities outside of the organization that administers the VPN. This may prevent or hinder the ability of an external specialist to join and contribute to a session where his or her expertise may be helpful.

SUMMARY OF THE CLAIMED SUBJECT MATTER

One aspect of the disclosure is a telehealth system comprising a public communications network (PCN), a plurality of provider access devices coupled to the PCN, and a plurality of patient access devices that can be controlled by any of the plurality of provider access devices. The plurality of patient access devices includes a first patient access device at a first location coupled to the PCN via a first local area network (LAN) and a first firewall and a second patient access device at a second location coupled to the PCN via a second LAN and a second firewall. The system also includes a monitoring server coupled to the PCN. The monitoring server receives status information from the plurality of patient access devices, wherein the status information includes presence information indicating the availability of the patient access device to participate in a communication session and device status of the patient access device. The system may also include a connectivity server coupled to the PCN. The connectivity server includes a database of connectivity rules, each connectivity rule including an identification of a healthcare provider and a location of patient access device the healthcare provider is authorized to access. The system may also include a plurality of geographically dispersed communications servers coupled to the PCN. Each of the plurality of communication servers has a network address on the PCN and is configured to establish a two-way audio/video communication session between one of the provider access devices and one of the patient access devices. At least one of the plurality of communications servers receives and maintains at least a portion of the database of connectivity rules from the connectivity server and the first communication firewall and the second communication firewall are configured to allow incoming communications from the network addresses of at least one of the plurality of communication servers. The provider access device transmits the identification of a healthcare provider to the communications server and receives from the communications server a list of patient access device locations that the healthcare provider is authorized to access and a status of each patient access device at each of the received locations. The provider access device receives a selection of a patient access device location from the healthcare provider and communicates the selected location to an optimal one of the plurality of communications servers. The optimal communications server establishes a communication session between the provider access device and the patient access device at the selected location. In addition, the monitoring server stores information regarding the established communication session in a reporting database.

DETAILED DESCRIPTION

Figure 1:
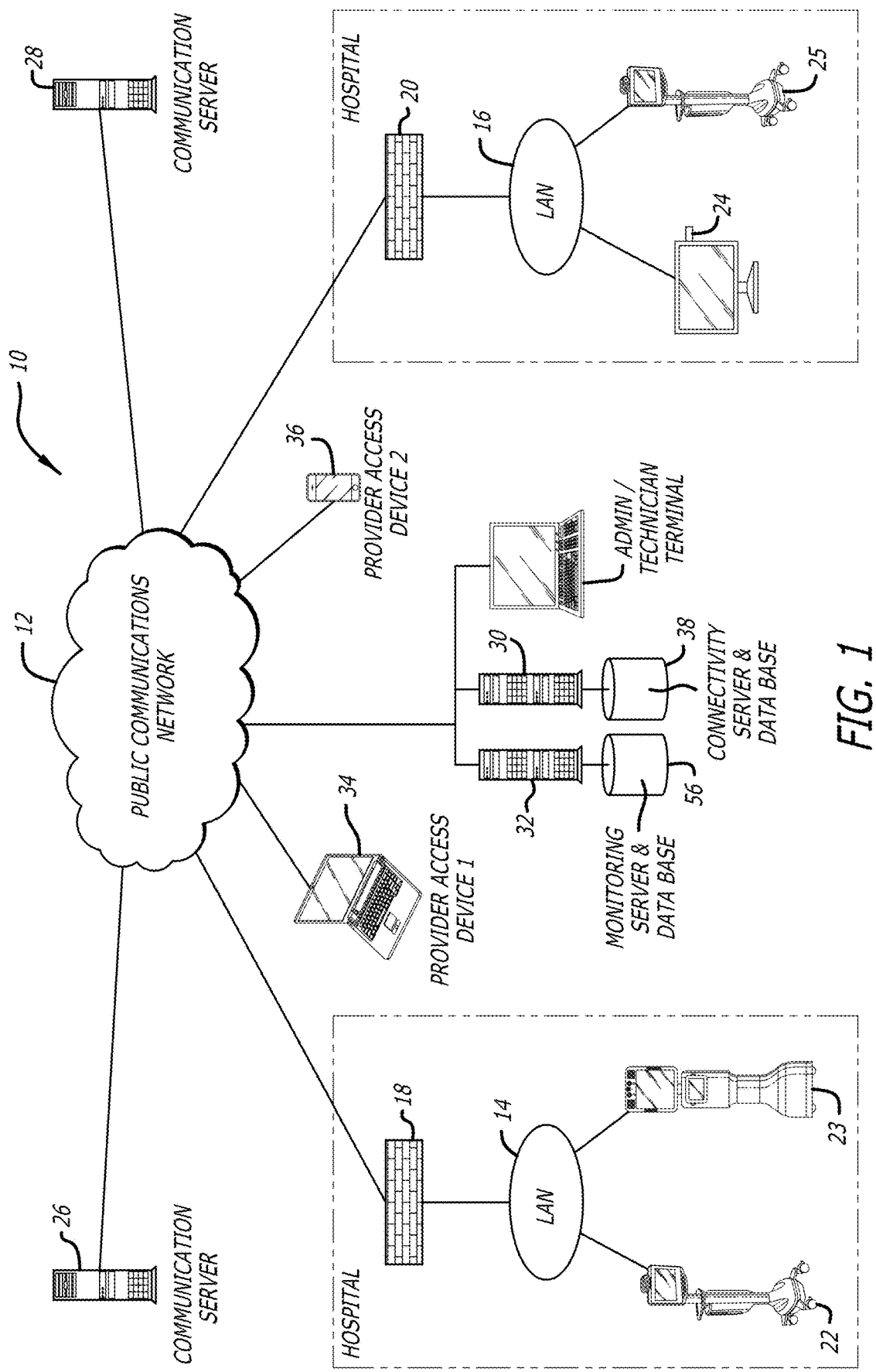
FIG. 1 illustrates an exemplary telehealth platform.

FIG. 1 illustrates an example of a telehealth platform 10. The platform may include a public communications network (PCN) 12, such as the Internet, that connects numerous local-area networks (LANs) 14, 16. Each LAN 14, 16 may be coupled to the PCN 12 via a communications firewall 18, 20. One or more patient access devices 22-25 may be coupled to each LAN 14, 16. A patient access device may also be coupled to the PCN 12 via a wide-area network (WAN), such as a cellular communications network (not shown). The platform may include a plurality of communications servers 26, 28, a connectivity server 30, and a monitoring server 32 coupled to the PCN. The platform may also include one or more provider access devices 34, 36 coupled to the PCN via a LAN or WAN (not shown). In general, the platform allows a physician or other healthcare provider to provide care to a patient by establishing a two-way audio/video communication between a patient access device 22-25 and a provider access device 34, 36. Although patient access devices 22-25 and provider access devices 24, 26 may be discussed as distinct and/or purpose-built devices, it is to be appreciated that the platform accommodates connections between generic users and/or devices.

Each LAN 14, 16 may be associated with a medical facility, such as a hospital, clinic, surgery center, primary care facility, ambulatory care center, or nursing home. A LAN could also be associated with a patient's home and/or the home or office of a care provider, such as a physician, clinician, nurse, or caretaker. For larger organizations, a LAN could take the form of a wide-area network (WAN) that connects multiple LANs. The LAN or WAN associated with each medical facility may also employ or otherwise support one or more virtual private networks (VPNs). However, the managed network architecture of the platform 10 generally eliminates the need for VPNs.

Each LAN 14, 16 may be coupled to the public communications network 12 via a firewall 18, 20. Each firewall 18, 20 may be configured by an administrator to allow incoming connections from one or more IP addresses representing the IP addresses of one or more of the communication servers 26, 28, the monitoring server 32, and/or the connectivity server 34. For example, the administrator may be provided with a list of trusted IP addresses and/or port numbers associated with the telehealth platform 10 and configure the firewall 18, 20 to accept connections from these IP addresses and/or ports.

An exemplary patient access device 22-25 may take the form of any device that allows the user of the provider access device to see and hear the patient. Preferably, the patient access device also allows the patient to see and hear the provider. In one embodiment, a patient access device may take the form of a telemedicine cart 22, 25 including a camera, a monitor, a microphone, and a speaker. In another embodiment, a patient access device could be a mobile telepresence robot 23 that includes a camera, a monitor, a microphone, and a speaker, as well as a mobile base that can be controlled by the remote healthcare provider using the provider access device. In yet another embodiment, the patient access device 24 could take the form of a small form factor computing device that executes a patient access device software program and is coupled to a camera, a monitor, a microphone, and a speaker via input/output ports on the computing device. One such small form factor computing device is the COMPUTE STICK, manufactured by INTEL Corporation. Alternatively, the patient access device may take the form of videoconferencing enabled tablet, smartphone, or laptop or desktop computer executing a patient access device software program. Additional examples of patient access devices include INTOUCH VITA, INTOUCH LITE, INTOUCH VANTAGE, INTOUCH XPRESS, INTOUCH VICI, and INTOUCH TV, all marketed by INTOUCH TECHNOLOGIES, INC., of Goleta, California. The details of various examples of provider access devices may be found in the follow U.S. patent and application publication numbers, the contents of which are hereby incorporated by reference: U.S. Pat. Nos. 6,925,357; 7,158,859; 8,515,577; 8,670,017; 8,718,837; 8,996,165; 9,198,728; 2009/0240371; and 2011/0213210.

An exemplary provider access device 34, 36 may take the form of any laptop or desktop computer, tablet, smartphone, or videoconferencing device including a camera, a monitor, a microphone, and a speaker. The provider access device may include a provider access software program that, when launched, provides an integrated application and user interface for accessing, controlling, or otherwise communicating with patient access devices 22-25 in order to treat a patient remotely. In addition, the provider access software may include the ability to launch a clinical documentation tool the physician can use to document the patient encounter, either within the provider access interface or within a separate application window launched from within the provider access software interface. The clinical documentation tool may be integrated with a hospital medical records system. The provider access software may also allow the provider to retrieve and view medical images of the patient, such as PACS images from MRIs or CT scans that have been performed on the patient. The provider access software may allow the provider to view these images within the application window of the provider access software or within a separate application window launched from within the provider access software interface.

In an alternative embodiment, the provider access device 34, 36 may simply employ a web browser that the user directs to a URL having a web-based provider access software application. This embodiment avoids the need to have a native application installed on the provider access device.

In yet another embodiment, both platform 10 may include a cloud-based telehealth portal configured to host telehealth sessions between any videoconferencing enabled devices via web browsers directed to and authenticated with the telehealth portal.

In general, the provider access software interface may include a variety of layouts and features as described in the following U.S. patent and application publication numbers, the contents of which are hereby incorporated by reference: U.S. Pat. Nos. 8,179,418; 8,849,680; 9,361,021; 9,098,611; 2005/0204438; and 2006/0052676. In addition, the provider access software interface may be customized depending on the type of patient access device the user chooses to connect to, as described in U.S. Pat. No. 8,897,920, the contents of which are hereby incorporated by reference.

The platform may include one or more geographically dispersed communications servers 26, 28 coupled to the public communications network 12. An exemplary communication server may operate as a session initiation protocol (SIP) server or similar protocol for signaling and controlling multimedia communication session over the internet. Each of the communications server 26, 28 is configured to facilitate a multimedia communication sessions between a provide access device 34, 36 and a patient access device 22-25 and/or to facilitate communication between a patient or provider access device and other servers coupled to the PCN, or between other servers themselves. The other servers could include another communications server, the monitoring server 32, the connectivity server 30, an authentication server, a medical records server, a billing server, a reporting server, or the like. In a platform with multiple, geographically dispersed communications servers 26, 28, an optimal server to facilitate a session between a provider access device 34, 36 and a patient access device 22-25 may be selected based on server load and/or network conditions such as latency, available link bandwidth, and/or round-trip time.

The connectivity server 30 maintains a database 38 of connectivity rules that control access throughout the platform. Each connectivity rule may specify a user and a location. A user may correspond to a medical care provider. A location in this context is a unique identifier that may represent the name of the location of a specific patient access device. For example, if the device is the only patient access device located in the emergency department of Mercy General Hospital in Asheville, NC, the location may be named "Mercy General, Ashville, ED." A connectivity rule may indicate that a "Dr. Jim Norris" can connect to or otherwise access the patient access device located at "Mercy General, Ashville, ED." The location may be distinct and/or decoupled from the name of the hospital or facility, the customer, the physical location of the device (in terms of latitude and longitude), and/or the device ID or serial number.

The database 38 of connectivity rules may be maintained by an administrator via a web portal that allows the administrator to add, delete, or otherwise modify connectivity rules. For example, when a new doctor is registered and obtains an account on the telehealth platform 10, one or more connectivity rules may be added to the database 38, with each rule specifying the doctor's username and a patient access device location he or she is authorized to access. A single provider may have access to numerous patient access devices located throughout one or more hospitals, hospital networks, or other care locations. In such cases, the database 38 may include a separate rule for each patient access device location the provider is authorized to access. In other embodiments, a single connectivity rule for a provider could specify a group of patient access devices the provider is authorized to access. A provider may not be able to connect to a patient access device location if there is no corresponding connectivity rule associating the provider with the patient access device.

In one embodiment, connectivity between users and locations may be grouped or otherwise managed according to "programs" maintained in the connectivity database 38. A program may be a unique name representing a set of users that have access to the devices at a set of locations for a particular purpose. For example, a major hospital with several neurologists on staff may contract with several smaller hospitals in remote locations to provide stroke tele-consults at the remote locations. Once telehealth endpoints are installed or otherwise made available at the remote hospitals, a program may be created in the database that includes the neurologists at the major hospital in the users list and the locations of the telehealth devices at each of the remote hospitals in the locations list. This grouping may automatically create rules in the connectivity server that allow each user in the users list to have access to each location in the locations list.

Figure 2:
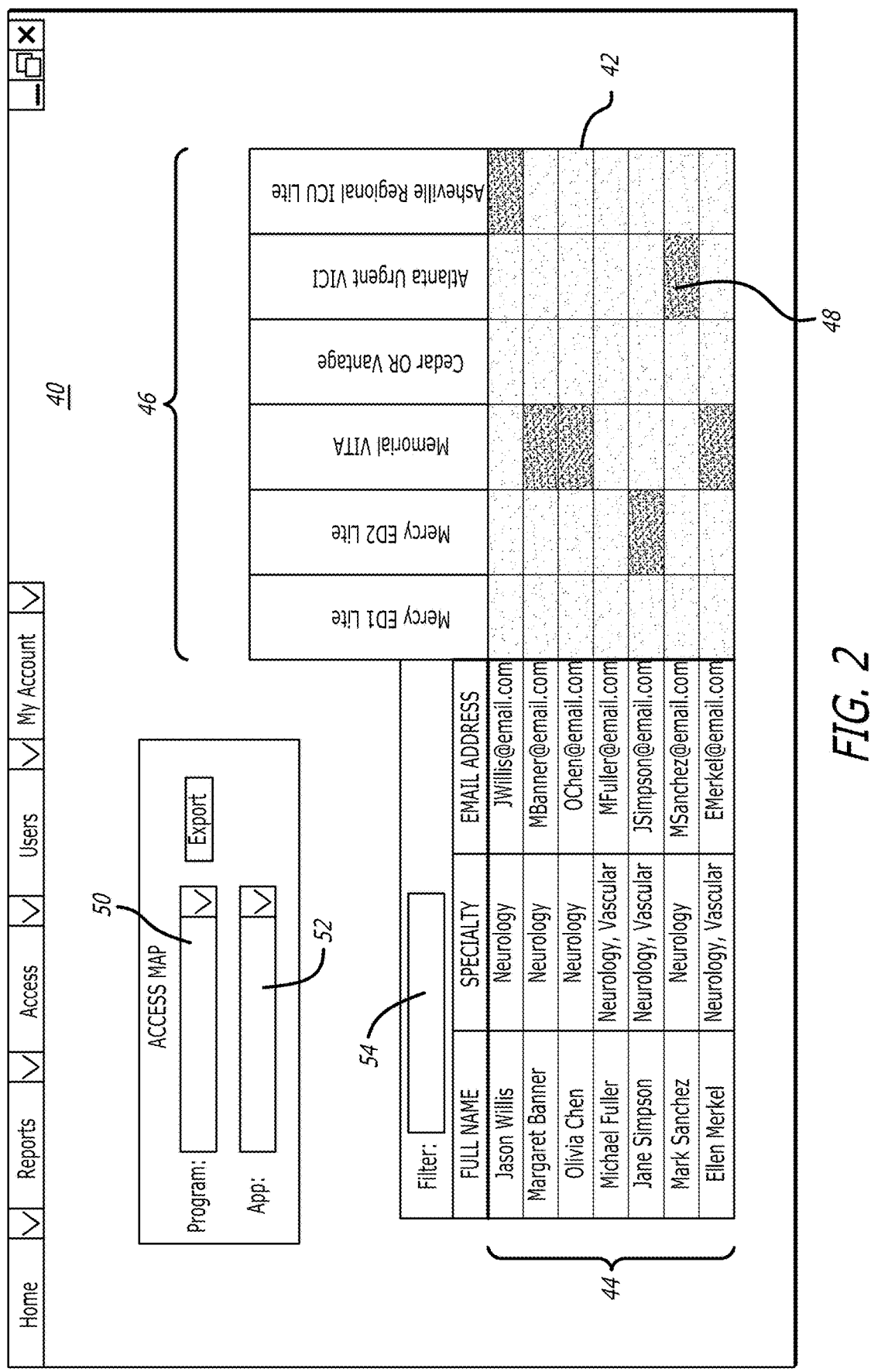
FIG. 2 illustrates an exemplary interactive access map.

The connectivity server 30 may provide a graphical user interface 40 that includes an interactive access map for each program. FIG. 2 shows an example of an interactive access map 42 for a stroke program associated with a Mercy General hospital. The map includes a vertical list 44 of the names and specialties of users on the left that have been added to the users list of the Mercy General stroke program. The map 42 also includes a horizontal list 46 of locations that have been added to the locations list of the Mercy General stroke program. By default, every user in the users list 44 of a program may have access to every location in the locations list 46 of that program. However, in one embodiment, the access map may allow access between specific users and locations to be toggled. For example, as shown in FIG. 2, connectivity is enabled for all of the tiles (each representing a combination of a user and a location) filled gray. However, connectivity has been disabled at one location for each user, as illustrated by the tiles filled black 48. An administrator may toggle connectivity for any user-location combination by clicking on the corresponding tile. The system may also allow the administrator to toggle the connectivity of several users and locations at once using a "CTRL-click" input on various tiles or dragging and highlighting a group of contiguous tiles using a mouse or keyboard input.

The administrator may select different access maps by selecting different programs from the drop-down menu 50 labelled "Program" in the upper-left corner of the interface. The interface may also include another drop-down menu 52 labelled "App" in the upper-left corner that allows the administrator to view access among users and locations across different applications, such as access to remote presence (e.g., two-way audiovisual sessions), access to clinical documentation tools, and/or access to medical records or imagery. The access map may additionally include a filter function 54 to allow the administrator to filter the list of user or locations to find specific users or locations more easily.

The monitoring server 32 maintains a database 56 of status information from each of the patient access devices 22-25. The status information may be reported to the monitoring server 32 from the patient access devices 22-25 periodically, in response to polling by the monitoring server, or in response to an event. Exemplary status information may include detailed device status information, including battery life, LAN ID and connection status, wireless signal strength, whether the device is coupled to a charging station and/or AC power, software version, date and time of last reboot, and other device-related information. The monitoring server 32 also maintains a record of all communications sessions between a patient access device and a provider access device, including the patient access device location and/or device ID, the provider username or ID, the duration of the session, the quality of the session, and other session-related information.

All or a portion of the database 38 of connectivity rules maintained in the connectivity server 30 is mirrored in one or more of the communication servers 26, 28. When a user or care provider wishes to connect to a patient access 22-25 device to conduct a session with a patient, he or she launches a provider access software program on his or her provider access device 34, 36. In another embodiment, the provider may simply direct a web browser to a web-based provider access interface. The user supplies login credentials, such as a username and password, which are transmitted to the communications server for authentication, or to a separate authentication server in communication with the communications server. Once the user is authenticated, the communications server sends to the provider access device a list of patient access devices to which the provider is permitted to connect, as well as a status of each of the devices at the corresponding locations. The device statuses may include ready, busy, and/or offline, depending on whether the device is online and available to participate in a communication session, online but in use by another provider, or offline, respectively.

From the displayed list of patient access devices the provider may then select an available patient access device to connect to, after which the provider access device transmits a request to connect to the patient access device to the communications server. The communications server then begins a process to the establish a communication session between the provider access device and the patient access device. The communications server may employ a process such as that described in U.S. Pat. No. 9,160,783, the contents of which are hereby incorporated by reference. In general, the communication server may first attempt to establish a peer-to-peer session between the patient and provider access devices using firewall traversal techniques such as UDP hole punching and/or those described in ICE/STUN/TURN protocols. If a peer-to-peer session cannot be established between the patient and provider access devices, the server may then attempt to establish a session using itself or another TURN server as a media relay server that relays media back and forth between the patient and provider access devices. In addition, the patient and provider access devices may employ a dynamic bandwidth allocation scheme in order to maximize the quality of the audio/video session through changing network conditions. The dynamic bandwidth allocation scheme may include that described in U.S. Pat. No. 9,264,664, the contents of which are hereby incorporated by reference.

The details of each communication session are logged in the monitoring server 32 and made available to a reporting server. The details of each session may include a username or other identification of the provider, the patient access device location, a serial number or identification of the patient access device, the type of patient access device, the duration of the session, whether the provider accessed the patient's medical records, and/or whether the provider accessed the patient's medical imagery. The identification of the provider may itself be associated with additional details about the provider, such as whether the provider is a part of one or more groups of providers or other healthcare organizations, the name of any such group of providers, and/or the provider's medical specialty or specialties. Similarly, each patient access device location may be associated with additional details regarding the patient access device location, such as the owner, custodian, and/or customer associated with the patient access device location, whether the location is associated with one or more hospitals or healthcare organizations, the name of any such the healthcare organizations, the physical location of the patient access device location, one or more service lines or medical specialties the patient access device is assigned to.

The reporting server may be configured to join usage data of providers and/or patient access device locations with details about each to generate interactive dashboards and reports for visualizing various aspects of the utilization of the telehealth platform. Details of this utilization reporting can be found in U.S. Pat. Nos. 8,902,278 and 9,251,313, the contents of which are hereby incorporated by reference.

The monitoring server may be configured to generate reports including patient access devices and their associated device health information for review by a technician at a remote terminal coupled to the PCN. The monitoring server may additionally be configured to analyze the device health data received form the patient access devices and detect an abnormal condition in one or more of the patient access devices. The analysis of the device health data may include artificial intelligence techniques such as unsupervised or supervised machine learning for anomaly detection. When the monitoring server detects an abnormal condition, the monitoring server may generate an alert to a technician identifying the patient access device requiring attention. Alternatively, the monitoring server may attempt to alleviate the abnormal condition by automatically performing a corrective action. In one embodiment, before generating an alert for a technician, the monitoring server may trigger a reboot for a patient access device that has been identified as having an abnormal condition. In some cases, rebooting the patient access device may correct the abnormal condition and alleviate the need for a technician to service the device.

Although the various servers such as the communications servers, monitoring server, connectivity server, and their associated databases may be illustrated or described as being separate devices, it is to be appreciated that any combination of their respective functionalities could be combined or hosted on a single or any number of physical devices coupled to the public communications network.

Additionally, as will be appreciated by one of ordinary skill in the art, principles of the present disclosure may be reflected in a computer program product on a computer-readable storage medium having computer-readable program code embodied in the storage medium, the computer-readable program code executable by a processor. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

While certain exemplary embodiments have been described and shown in the accompanying drawings, it is to be understood that such embodiments are merely illustrative and not restrictive on the broader disclosure, and that this disclosure not be limited to the specific constructions and arrangements shown and described, since various other modifications may occur to those ordinarily skilled in the art.

What is claimed is:

1. A telehealth system, comprising:
a public communications network (PCN);
a plurality of provider access devices coupled to the PCN;
a plurality of patient access devices that can be controlled by any of the plurality of provider access devices, the plurality of patient access devices including a first patient access device at a first location coupled to the PCN via a first local area network (LAN) and a first firewall and a second patient access device at a second location coupled to the PCN via a second LAN and a second firewall;
a monitoring server coupled to the PCN, the monitoring server receives status information from the plurality of patient access devices, wherein the status information includes presence information indicating the availability of the patient access device to participate in a communication session and device status of the patient access device;
a connectivity server coupled to the PCN, the connectivity server includes a database of connectivity rules, each connectivity rule including an identification of a healthcare provider and a location of patient access device the healthcare provider is authorized to access; and,
a plurality of geographically dispersed communications servers coupled to the PCN, each of the plurality of communication servers has a network address on the PCN and is configured to establish a two-way audio/video communication session between one of the provider access devices and one of the patient access devices, wherein,
at least one of the plurality of communications servers receives and maintains at least a portion of the database of connectivity rules from the connectivity server;
the first communication firewall and the second communication firewall are configured to allow incoming communications from the network addresses of at least one of the plurality of communication servers;
the provider access device transmits the identification of a healthcare provider to the communications server and receives from the communications server a list of patient access device locations that the healthcare provider is authorized to access and a status of each patient access device at each of the received locations;
the provider access device receives a selection of a patient access device location from the healthcare provider and communicates the selected location to an optimal one of the plurality of communications servers;
the optimal communications server establishes a communication session between the provider access device and the patient access device at the selected location; and,
the monitoring server stores information regarding the established communication session in a reporting database.

2. The system of claim 1, wherein the system includes at least two geographically dispersed communications servers coupled to the PCN, and a first communications server acts as a master communications server and a second communications server acts as a proxy communications server between the master communications server and one of the provider access device and the patient access device.

3. The system of claim 2, wherein the second communications becomes the master communications server when the first communications server fails.

4. The system of claim 1, wherein the monitoring server generates a prioritized list of patient access devices based on the respective health metrics of the patient access devices.

5. The system of claim 1, wherein the connectivity server generates an interactive connectivity map based on the plurality of connectivity rules.

6. The system of claim 5, wherein interactive connectivity map can be displayed and edited by an administrator from a remote terminal coupled to the PCN.

7. The system of claim 6, wherein the interactive connectivity map includes a first axis including identifications of a plurality of medical providers and a second axis including identifications of patient access device locations.

8. The system of claim 7, wherein the identification of at least one of the plurality of healthcare provider is associated with an identification of a group of healthcare providers.

9. The system of claim 8, wherein the medical provider axis of the interactive connectivity map can be filtered based on the associated group of healthcare providers.

10. The system of claim 7, wherein the identification of at least one of the plurality of patient access device locations is associated with an identification of a healthcare organization.

11. The system of claim 10, wherein the patient access device location axis of the interactive connectivity map can be filtered based on the associated healthcare organization.

12. The system of claim 1, wherein the optimal one of the plurality of communication servers is chosen based on at least one of server proximity, server load, and network conditions.

13. The system of claim 1, wherein the one or more device health metrics includes at least one of battery life, LAN connection status, wireless network strength, cellular network connection status, device location, time of last device reboot, whether the device is connected to a charging station, whether the device is coupled to AC power, and/or software version.

14. The system of claim 13, wherein the monitoring server is configured to detect an abnormal condition of a patient access device.

15. The system of claim 14, wherein the monitoring server is configured to trigger a reboot of the patient access device in response to detecting the abnormal condition.

16. The system of claim 14, wherein the monitoring server is configured to alert a technician in response to detecting the abnormal condition.

17. The system of claim 1, wherein the patient access device periodically transmits a message to the communications server when the patient access device is not in a communication session.

18. The system of claim 17, wherein the patient access device transmits the message to the communications server in response to a message sent from the communications server.

* * * * *